United States Patent [19]

Bins

[11] Patent Number: 4,777,044

[45] Date of Patent: Oct. 11, 1988

[54] THERAPEUTIC PREPARATION HAVING AMMONIUM NITRATE AS ITS ACTIVE SUBSTANCE

[76] Inventor: Jan W. Bins, Buitenrustplein 8, 2271 HD Voorburg, Netherlands

[21] Appl. No.: 96,303

[22] Filed: Sep. 9, 1987

Related U.S. Application Data

[63] Continuation of Ser. No. 771,859, Sep. 3, 1985, abandoned.

[30] Foreign Application Priority Data

| Jun. 4, 1984 | [NL] | Netherlands | 8401782 |
| Mar. 13, 1985 | [BE] | Belgium | 0/214.637 |
| Jun. 3, 1985 | [EP] | European Pat. Off. | 85200870.5 |

[51] Int. Cl.$^4$ .................... A61K 9/28; A61K 33/02
[52] U.S. Cl. .................................................. 424/166
[58] Field of Search .......................................... 424/166

[56] References Cited

U.S. PATENT DOCUMENTS 4,466,960  8/1984  Silverman et al. ............... 424/166

Primary Examiner—Shep K. Rose
Attorney, Agent, or Firm—Blum Kaplan

[57] ABSTRACT

A dry compressed ammonium nitrate tablet of solid ammonium nitrate and an auxilliary tabletting material is coated to enhance the paletability of the ammonium nitrate. Auxilliary tabletting substances include filling agents, binding agents, agents to stimulate disintegration of the tablets and lubricating agents. The ammonium nitrate tablets are particularly well suited for lowering the pH of urine.

11 Claims, No Drawings

THERAPEUTIC PREPARATION HAVING AMMONIUM NITRATE AS ITS ACTIVE SUBSTANCE

This is a continuation of application Ser. No. 771,859, filed Sept. 3, 1985, now abandoned.

SUMMARY OF THE INVENTION

Compressed tablet consisting of solid ammonium nitrate and auxiliary tabletting substances, with a coating.

The invention relates to a therapeutic preparation having ammonium nitrate as its active substance.

Ammonium nitrate is known as an agent that lowers the pH, of urine so that the conditions for the forming of renal calculi and infections in the urinary tract are much less suited.

In general a solution of ammonium nitrate in water is used for this purpose; this solution can easily be prepared, due to the good solubility of ammonium nitrate, and it is stable. Said solutions have a highly disagreeable taste.

Many attempts have been made to process ammonium nitrate to preparations which do not show this objection, e.g. by adding flavourings to solutions of ammonium nitrate. However, no flavourings have been found which sufficiently disguise the highly unpleasant taste of ammonium nitrate.

It has now been invented, that ammonium nitrate can be compressed into tablets with the commonly used auxiliary substances and that by coating these tablets with coating substances, coated tablets are obtained, which do not have the unpleasant taste of ammonium nitrate.

Thus a prejudice has been overcome; until now it was generally assumed that ammonium nitrate could not be compressed into tablets because of the known explosive nature of ammonium nitrate.

The preparation according to the invention is therefore characterized in that it comprises a compressed tablet consisting of solid ammonium nitrate, and auxiliary tabletting substances with a coating of lacquer or sugar.

It is suitable that each coated tablet contains 250 to 1000 mg of ammonium nitrate.

The manufacture and coating of the tablets is carried out in the usual way and with commonly used auxiliary substances.

Auxiliary tabletting substances are e.g. filling agents, binding agents, agents which stimulate disintegration of tablets, and lubricating agents.

Examples of such agents are: starch, originating from patatoes, maize, rice or otherwise, lactose directly compressable or not calcium compounds, directly compressable or not, micro crystalline cellulose, glucose, saccharose, mannitol, sorbitol, colloidal, silicon dioxyde, talcum, magnesium stearate, cellulose derivatives, cross-linked polyvinyl pyrrolidon (PVPP).

Combinations of micro crystalline cellulose and anorganic auxiliary tabletting substances, e.g. colloidal silicon dioxide or talcum are very suitable, because with these substances tablets can be manufactured to the level of hardness which gives the best results when coated.

Preferably one should start from a mixture of ammonium nitrate, micro crystalline cellulose, colloidal silicon dioxide and a lubricating agent e.g. magnesium stearate.

The ratio of the auxiliary components is chosen in a usual way, for instance 5%–50% micro crystalline cellulose, based upon $NH_4NO_3$, 0.05%–10% colloidal silicon dioxide, based upon $NH_4NO_3$, 0.1%–2% lubricating agent, based upon $NH_4NO_3$.

Preferably the amount of micro crystalline cellulose should be between 17.5% and 22.5% and the amount of colloidal silicon dioxide between 0.1% and 0.3%, both based upon $NH_4NO_3$, because this gives the best results for tabletting.

The preparation of the starting mixture and the process of compression must take place in a dry surrounding because of the hygroscopic nature of ammonium nitrate. Preferably said processes should take place in air with a relative humidity of at most 40%, or rather of 30%–35%.

Compressing to tablets should preferably take place under a pressure that ensures that the tablets formed have a hardness of at least 15 kp, as measured by the Heberlein hardness tester. In this way tablets are obtained which are suitable for final coating.

For coating the usual substances can be used, such as methacryl compounds, waxes and resins (synthetic or non-synthetic), cellulose and its polymers, particularly cellulose acetopropionate (CAP), shellac etc.

The coating can have the usual thickness. A layer of acid resistant lacquer equivalent to 2 mg to 10 mg per $cm^2$ surface of the tablet is very suitable.

The invention is elucidated by means of the following example.

EXAMPLE

In a room with a relative humidity of 35% 10 kg of ammonium nitrate was rubbed with 1.82 kg micro crystalline cellulose, (Avicel pH 102 ®) and with 60 g colloidal silicium dioxide (Aerosil ®) in a mixing vessel for 20 minutes.

Thereupon 120 g of magnesium stearate was added and the whole was mixed again for a few minutes.

From the mixture thus obtained convex tablets were prepared having a diameter of 11 mm, and containing 500 mg of ammonium nitrate per tablet. The hardness of the tablets was 20 kp, measured by the Heberlein hardness tester.

Said tablets were then provided with a coating.

For this purpose they were put into a coating pan, whereupon they were sprayed in the usual way with a suspension of: acid resistant coating lacquer

| | |
|---|---|
| (Eudragit L 12.5 p ®) | 2624 g ~ 328 g dry substance |
| dibutylphthalate | 16 g ~ 16 g dry substance |
| pigment suspension | 3334 g ~ 1000 g dry substance |
| 1:1 mixture of acetone: isopropanol | 8026 g |
| | 14000 g ~ 1344 g dry substance |

The pigment suspension consisted of:

| | |
|---|---|
| talcum | 560 g |
| magnesium stearate | 80 g |
| titane dioxide | 480 g |
| polywax 6000 (33% dispersion in water) | 240 g |
| isopropanol | 2640 g |

| -continued |
| --- |
| 4000 g with 30% solid substance |

The tablets were provided with a coating layer with a weight of 20.5 mg/cm$^2$.

The dry substance content originating from the lacquer was 5 mg/cm$^2$.

The coated tablets were tested for their resistance against gastric acid according to USP XX with artifical gastric juice pH 1.2.

The coating layer lasted for 60 minutes.

The coated tablets were also tested for their behaviour in artificial intestinal juice (according to USP XX, pH 7.5).

In this artificial intestinal juice they disintegrated after 6 to 7 minutes.

I claim:

1. A dry compressed ammonium nitrate tablet prepared by:
   preparing a tablet mixture of a therapeutic agent consisting essentially of solid ammonium nitrate and auxiliary tabletting material;
   dry compressing the tablet mixture to form a tablet; and
   coating the dry compressed tablet to enhance the palatability of the ammonium nitrate.

2. The therapeutic preparation of claim 1, wherein ammonium nitrate is present in an amount of between about 250 and 100 mg per tablet.

3. The therapeutic preparation of claim 1, wherein the auxiliary tabletting substances include micro crystalline cellulose, colloidal silicon dioxide and a lubricating agent.

4. The therapuetic preparation of claim 1, wherein the auxiliary tabletting substances include
   5%–50% micro crystalline cellulose
   0.05%–10% colloidal silicon dioxide
   0.01%–2% lubricating agent
based upon ammonium nitrate.

5. The therapeutic preparation of claim 4, wherein the auxiliary tabletting substances include
   17.5%–22.5% microcrystalline cellulose
   0.1%–0.3% colloidal silicon dioxide
based upon ammonium nitrate.

6. The therapuetic preparation of claim 1 or 4, wherein the tablet has a hardness of at least 15 kp, measured by the Heberlein hardness tester.

7. The therapeutic preparation of claim 1 or 4, wherein the coating consists of an acid-resistant lacquer.

8. The therapeutic preparation of claim 7, wherein the coating layer consists of 2 mg to 10 mg per cm$^2$ of the tablet surface of acid-resistant lacquer.

9. The tablet of claim 1, wherein the coating delays action on the tablet by humidity.

10. A method of administering a solid anti-renal calculi formation medication to a patient, comprising administering to a patient a tablet consisting essentially of solid ammonium nitrate and auxiliary tabletting material which has been dry compressed to form the tablet and coated to enhance the palatability of the ammonium nitrate.

11. A method of administering a solid anti-urinary tract infection medication to a patient, comprising administering to a patient a tablet consisting essentially of solid ammonium nitrate and auxiliary tabletting material which has been dry compressed to form the tablet and coated to enhance the palatability of the ammonium nitrate.